(12) United States Patent
Neumann et al.

(10) Patent No.: US 8,802,897 B2
(45) Date of Patent: Aug. 12, 2014

(54) METHOD FOR PREPARING CYCLIC KETONES

(71) Applicant: Alessa GmbH, Frankfurt (DE)

(72) Inventors: Doris Neumann, Offenbach (DE); Joachim Ritzer, Rodenbach (DE); Gunther Effenberger, Bad Vilbel (DE)

(73) Assignee: Allessa GmbH, Frankfurt (DE)

( * ) Notice: Subject to any disclaimer, the term of this patent is extended or adjusted under 35 U.S.C. 154(b) by 0 days.

(21) Appl. No.: 13/712,037

(22) Filed: Dec. 12, 2012

(65) Prior Publication Data

US 2013/0165697 A1     Jun. 27, 2013

(30) Foreign Application Priority Data

Dec. 24, 2011  (EP) .................................. 11010207

(51) Int. Cl.
*C07C 45/00*  (2006.01)

(52) U.S. Cl.
USPC .......................................... 568/362

(58) Field of Classification Search
CPC ........................ C07C 45/006; C07C 49/403
USPC .......................................... 568/362
See application file for complete search history.

(56) References Cited

U.S. PATENT DOCUMENTS

| | | | |
|---|---|---|---|
| 2,829,166 A | 4/1958 | Joris et al. | |
| 4,409,401 A | 10/1983 | Murtha | |
| 5,886,232 A | 3/1999 | Landscheidt et al. | |
| 6,015,927 A | 1/2000 | Kiel | |
| 6,046,365 A | 4/2000 | Kiel | |
| 6,215,028 B1 * | 4/2001 | Oster et al. | 568/362 |
| 2010/0041714 A1 | 2/2010 | Blanc et al. | |

FOREIGN PATENT DOCUMENTS

| | | |
|---|---|---|
| DE | 2909780 A1 | 9/1980 |
| EP | 0731075 A1 | 9/1996 |
| EP | 0822173 A1 | 2/1998 |
| EP | 0889019 A1 | 1/1999 |
| EP | 0890565 A1 | 1/1999 |
| EP | 0913376 A1 | 5/1999 |
| JP | 11060534 | 3/1999 |

OTHER PUBLICATIONS

Higashijima, et al., Effects of Alcoholic Solvents on the Formation of Cyclohexanones in the Hydrogenation of Phenols over Pd-C Catalysts, Bulletin of the Chemical Society of Japan, 1992, 2955-2959, 65, The Chemical Society of Japan.
Takagi, et al., Effects of Solvents on the Hydrogenation of Mono-Aromatic Compounds Using Noble-Metal Catalysts, Energy & Fuels, 1999, 1191-1196, 13, American Chemical Society.
Wydra, et al., Die selektive Hydrierung von 4-substituierten Phenolderivaten zu den Cyclohexanon-Analogen-Katalysatoroptimierung und Kinetik, Chemie Ingenieur Technik, Jun. 2002, 800-804, 74-6, Wiley-VCH Verlag GmbH, Weinheim, Fed. Rep. of Germany.
International Search Report dated Mar. 15, 2013.

* cited by examiner

*Primary Examiner* — Sikarl Witherspoon
(74) *Attorney, Agent, or Firm* — Michael W. Ferrell; Ferrells, PLLC; Anna L. Kinney

(57) ABSTRACT

A method for hydrogenating optionally substituted phenols with one hydroxyl group to cyclohexanones over modified, palladium-comprising supported catalysts. This is possible surprisingly in selected alcoholic solvents with high selectivity. Here it is even possible to recycle the catalysts employed, which hitherto has only been possible with considerable loss of selectivity.

20 Claims, No Drawings

METHOD FOR PREPARING CYCLIC KETONES

CLAIM FOR PRIORITY

This application is based on European Priority Application No. EP 11010207 filed Dec. 24, 2011, entitled "Verfahren zur Herstellung von cyclischen Ketonen", the priority of which is hereby claimed and the disclosure of which is incorporated herein by reference in its entirety.

TECHNICAL FIELD

The present invention relates to a method for preparing cyclic ketones, particularly cyclohexanones, by catalytic hydrogenation of the corresponding phenols.

BACKGROUND

It is known that phenols can be hydrogenated catalytically to cyclic ketones. U.S. Pat. No. 2,829,166 describes the hydrogenation of phenols in the presence of palladium catalysts to give the corresponding cyclohexanones. A method for hydrogenating p-tert-amylphenol is known from DE 29 09 780 A1. A method for preparing substituted cyclohexanones is disclosed in EP 731 075 A1. Furthermore, EP 889 019 A1 and EP 890 565 A1 disclose methods for preparing cyclohexanones by hydrogenation of the corresponding phenols in the presence of alkanes or water as solvent. The use of aliphatic alcohols as solvent is not disclosed in these documents.

Good selectivities for cyclohexanones are generally obtained at temperatures of 120-250° C. and a hydrogen pressure of 1-20 bar. In this case it may be advantageous to treat the Pd/C catalysts with an alkali metal carbonate or alkaline earth metal carbonate or other basic or neutral salts or to add basic or neutral salts to the hydrogenation mixture.

Solvents which can be used for the hydrogenation of phenols are however limited. Hydrogenation in the absence of solvent is described (cf. U.S. Pat. No. 2,829,166), however this is only feasible for phenols which melt in the range of the hydrogenation temperatures. The only other known solvents are ethers (cf. EP 731 075 A1), specific alkanes such as, for example, methylcyclohexane (cf. EP 889 019 A1) or ethers (cf. EP 890 565 A1). The catalytic hydrogenation of phenols in aromatic compounds as solvents, such as toluene or xylene for example, is further described by M. Wydra and H. Vogel in Chemie Ing. Techn. 74, 800-804, 2002.

A method for preparing hydroxycyclohexanones is known from JP 11-060534 A, in which substituted polyphenols, such as resorcinol, hydroquinone or pyrogallol, are hydrogenated in the presence of a palladium catalyst comprising alkali metal, in a saturated monohydric $C_3$—$C_{12}$-alcohol. The Pd catalyst may be generated for example by treatment with alkali metal hydroxides.

It is known that, when using relatively polar solvents such as, for example, alcohols, which would clearly broaden the range of application of this reaction, substantially lower turnovers and selectivities occur. For example, Tagaki et al. in Energy & Fuels 13 (6), 1191-1196, 1999 describe the ring hydrogenation of various aromatic compounds and found that, in the case of catalysis by Pt/C, the reactivity was greatly reduced by alcohols. Higashijima and Nishimura in Bull. Chem. Soc. Jpn. 65, 2955-2959, 1992 describe investigations relating to the ring hydrogenation of phenol and cresols over Pd/C catalysts in various solvents and found that in alcohols both the hydrogenation rate as well as the selectivity in favour of the cyclohexanones, had been considerably reduced in comparison to the hydrogenation in alkanes or without solvent. This effect has been found when using commerically available Pd/C catalysts for diverse primary, secondary and tertiary alcohols with 3 or more carbon atoms; the effect was somewhat weakened for acid treated Pd/C catalysts.

A method for the hydrogenation of phenols is disclosed in U.S. Pat. No. 4,409,401, in which a palladium catalyst specifically poisoned with sulfur is used. The preparation of the catalyst takes place by oxidative and subsequently a reductive treatment. This document states that during the hydrogenation it is advantageous for basic substances to be present, for example Na carbonate. The reaction can take place in the presence of a diluent. Examples of the latter are saturated and aromatic hydrocarbons, alcohols or the desired product of the method.

EP-A-822,173 discloses a method for preparing 1,3-cyclohexanediones. Starting from 1,3-bisphenols, a transfer hydrogenation method is carried out, in which a hydrogen donor, typically a secondary alcohol or formic acid or one of its salts, hydrogenates the starting material in the presence of a palladium catalyst. A classical hydrogenation by means of hydrogen is not disclosed.

US-A-2010/041714 relates to the preparation of bisarylaminotetralins. In one working example the preparation of a precursor of 5-hydroxy-3,4-dihydro-2H-naphthalen-1-one is described. This takes place by hydrogenation of 1,5-dihydroxynaphthalene in isopropanol and aqueous sodium hydroxide in the presence of a palladium catalyst supported on carbon. The proportions of palladium and of aqueous sodium hydroxide, based on the bisphenol used, are quite high in this example.

SUMMARY OF INVENTION

Surprisingly it has now been found that phenols with one hydroxyl group can be hydrogenated in relatively long-chain aliphatic and/or cycloaliphatic alcohols with high selectivity coupled with high turnover to give the corresponding cyclic ketones, if a specific catalyst is used for this purpose.

The present invention relates to a method for hydrogenating phenols with one hydroxyl group to cyclic ketones by reacting the phenols with hydrogen in the presence of a supported catalyst comprising palladium in an alcoholic solution, wherein an aliphatic and/or cycloaliphatic alcohol comprising at least three carbon atoms is used, and the supported catalyst comprising palladium has been treated prior to use with a neutral or basic salt, preferably an alkali metal salt and/or an alkaline earth metal salt and/or an ammonium salt and/or the hydrogenation takes place in the presence of a supported catalyst comprising palladium and a neutral or basic salt.

On conducting the method according to the invention, it has been found that good selectivities for cyclic ketones with high turnover of the phenols is generally obtained at temperatures of 80 to 250° C., preferably of 90 to 250° C., particularly preferably at 90 to 200° C. and most particularly preferably at 100 to 180° C.

The method according to the invention can be carried out at different hydrogen pressures. The selectivity and the turnover of the reaction are highest at a hydrogen pressure of 0.5-20 bar. Preferably the hydrogenation is carried out at 0.5-15 bar, particularly preferably at 1-10 bar.

The method according to the invention is characterised in that a monohydric phenol is dissolved in an aliphatic and/or cycloaliphatic alcohol with at least three carbon atoms, a supported Pd-comprising catalyst and a neutral or basic salt, or a supported Pd-comprising catalyst which has been modified with a neutral or basic salt, is added, and the monohydric phenol is reacted with hydrogen at the reaction temperature and optionally under pressure. The reaction takes place preferably in an autoclave.

Straight-chain or branched aliphatic and/or cycloaliphatic alcohols with at least three carbon atoms are used as alcoholic solvents. The latter are primary, secondary or tertiary aliphatic alcohols with at least three carbon atoms, preferably straight-chain or branched secondary or tertiary aliphatic alcohols with at least three carbon atoms. These alcohols can be straight-chain or branched-chain or else cyclic. Secondary or tertiary alcohols with three to eight carbon atoms are most particularly preferably used. Examples for this purpose are isopropanol, 2-butanol, tert-butanol, 2-pentanol, 3-pentanol, 2-methylbutan-2-ol, 3-methylbutan-2-ol, cyclopentanol, cyclohexanol, 2-methylpentan-2-ol, 2-methylpentan-3-ol, 3-methylpentan-2-ol, 3-methylpentan-3-ol, 4-methylpentan-2-ol, 2,3-dimethyl-2-butanol, 3,3-dimethyl-2-butanol, 2-hexanol, 3-hexanol, 2,2-dimethyl-3-pentanol, 2,3-dimethyl-3-pentanol, 2,4-dimethyl-3-pentanol, 4,4-dimethyl-2-pentanol, 3-ethyl-3-pentanol, 2-methyl-2-hexanol, 2-methyl-3-hexanol, 5-methyl-2-hexanol, 2-heptanol, 3-heptanol, isomeric methylcyclohexanols, 2-octanol, 3-octanol, 4-methylheptan-3-ol, 6-methylheptan-2-ol, 2-ethylhexanol and 3,7-dimethyl-3-octanol.

Examples of cycloaliphatic alcohols are cyclohexanol or methylcyclohexanol.

The dilution of the phenol in the corresponding alcoholic solvent is generally chosen to be 10 to 95%, preferably 20 to 90%, particularly preferably 25 to 85%.

In addition to the alcoholic solvent, the reaction mixture used according to the invention may also have further liquids miscible with the straight-chain or branched aliphatic and/or cycloaliphatic alcohols with at least three carbon atoms. A low proportion of water for example may thus be present, for example up to 20% by weight of water, preferably between 0.1 and 10% by weight of water, based on the total amount of solvent. The amount of further liquids miscible with the alcohols, particularly water, is chosen on a case-by-case basis, such that a monophasic system results and no separation takes place. The presence of water is preferred, particularly when the hydrogenation is conducted in the presence of a neutral or basic salt.

DETAILED DESCRIPTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

In the method according to the invention catalysts comprising supported palladium are used. A multitude of materials are suitable as supports, for example aluminum oxide, ceramic support materials or carbon or graphite. Support materials for these catalysts are known to those skilled in the art and are generally used in finely divided form, which may optionally be compressed into pellets. The support material used is particularly preferably carbon, particularly activated carbon.

The catalytically active metal is palladium or a combination of palladium with other metals, for example with platinum or rhodium.

The catalyst can be doped with other components besides the catalytically active metal, for example with alkali metals or alkaline earth metals.

These are generally catalytically active co-components.

Preference is given to the use of catalysts comprising palladium which have no catalyst poisons, particularly no inorganic and/or organic sulfur compounds, such as inorganic sulfides or hydrosulfides, or such as organic sulfides, disulfides, thioacids or mercaptans as well as heterocyclic sulfur compounds.

A palladium catalyst supported on carbon is most particularly used (hereinafter "Pd/C catalyst"). Any carbon supports may be used. These Pd/C catalysts are commercially available.

The supported catalyst generally comprises 1 to 15% by weight of catalytically active metal, preferably 1 to 10% by weight and most particularly preferably 1 to 5% by weight. It comprises preferably 1-10% precious metal, particularly preferably 1-5% precious metal. The supported catalysts can be used as solids, e.g. as powders or as pellets or else as water-moist pastes. The catalyst or catalysts are present in suspended form in the reaction mixture; the other constituents of the reaction mixture, such as the solvent or solvents, the phenol and the hydrogenated phenol, are generally present as a single-phase mixture, and form a solution which reacts with the hydrogen present in the gas phase.

These catalysts are used in amounts of $1\times10^{-4}$ to 1% by weight (calculated in each case as Pd metal), based on the phenol. Preferably they are used in amounts of $1\times10^{-3}$ to 1% by weight, particularly preferably in amounts of $1\times10^{-3}$ to 0.1% by weight.

The catalyst used in the method according to the invention is treated before use with a neutral or basic salt, generally with a solution of a neutral or basic alkali metal salt, alkaline earth metal salt or ammonium salt, or the neutral or basic salt is added to the hydrogenation mixture. In the latter case, it is also possible to use previously untreated supported catalysts. The neutral or basic salt can be added without solvent to the supported catalyst or preferably as a solution in a suitable solvent, particularly as an aqueous solution. The metal salts used as neutral or basic salts are preferably hydroxides, carbonates, hydrogen carbonates, phosphates, monohydrogen phosphates, formates, acetates, propionates or borates of alkali metals, such as lithium, sodium, potassium, rubidium or cesium; or of alkaline earth metals such as beryllium, magnesium, calcium, strontium or barium; or of ammonium. Particular preference is given to using hydroxides, carbonates, hydrogen carbonates, phosphates, monohydrogen phosphates, acetates or borates of lithium, sodium, potassium, magnesium, calcium, strontium or ammonium. Examples are hydroxides of lithium, sodium, potassium or ammonium; hydrogen carbonates of sodium, potassium or ammonium; carbonates of lithium, sodium, potassium, ammonium, magnesium or calcium; phosphates of lithium, sodium, potassium, ammonium or magnesium; formates of lithium, sodium, potassium, ammonium or calcium; acetates of lithium, sodium, potassium, ammonium or calcium; propionates of lithium, sodium, potassium, ammonium or calcium or borates of lithium, sodium, potassium or ammonium. Mixtures of neutral or basic salts can also be used.

In the context of the present invention, a neutral or basic salt is understood to mean a salt whose 0.1-15% aqueous solution has a pH of 7 or greater than 7.

This neutral or basic salt added to the catalyst and/or reaction solution is added in amounts of 0.001 to 5 mol %, based on the phenol used. The salt is added preferably in amounts of 0.005 to 5 mol %, particularly preferably in amounts of 0.005 to 1 mol %. The treatment or addition can take place with the salt in solution, for example in water or in alcoholic solvents.

The neutral or basic salt is preferably added as an aqueous solution to the supported catalyst or to the reaction mixture. To prepare the aqueous solution, the salt is generally dissolved in 1 to 1000-fold the amount of water, based on the salt. The proportion of water should be chosen such that the water forms a homogeneous mixture, and not a multiphase system, with the alcohol with at least three carbon atoms.

The supported palladium catalyst used in the method according to the invention may be fresh or a catalyst already used once, or more than once, may be used. Surprisingly, it has been shown that it is even possible to recycle the used catalysts, which has been possible only with considerable loss of selectivity for catalysts not treated in this manner or in the case of implementation in other solvents. The phenols used in the method according to the invention can be any compounds having at least one aromatic ring and one hydroxyl group covalently bonded to it.

The phenols can be mononuclear or polynuclear carbocyclic aromatic compounds, preferably trinuclear, binuclear or particularly mononuclear carbocyclic aromatic compounds; or they can be mononuclear or polynuclear heterocyclic aromatic compounds preferably having one or two ring heteroatoms selected from the group consisting of nitrogen, oxygen and sulfur or combinations thereof.

These carbocyclic or heterocyclic aromatic compounds have one phenolic hydroxyl group, and optionally one or more substituents, for example substituents selected from the group consisting of alkyl, alkoxy, hydroxyalkyl, cycloalkyl, cycloalkoxy, aryl, aryloxy, aralkyl, aralkyloxy, carboxylic acid, sulfonic acid, amino, nitro, carboxylic acid ester, carboxylic acid amide, sulfonic acid ester, sulfonic acid amide and/or nitrile groups or of combinations of two or more of these groups or atoms.

Carbocyclic or heterocyclic aromatic compounds with only one phenolic hydroxyl group are thus used.

Examples of alkyl groups are straight-chain or branched alkyl groups with one to ten carbon atoms, such as methyl, ethyl, propyl, isopropyl, n-butyl, sec-butyl, tert-butyl, pentyl, n-hexyl, n-heptyl, 2-ethylhexyl, n-octyl, n-nonyl or n-decyl.

Examples of alkoxy groups are those with straight-chain or branched alkyl groups with one to ten carbon atoms, such as methoxy, ethoxy, isopropoxy, n-butoxy, sec-butoxy, tert-butoxy, pentyloxy, n-hexyloxy, n-Heptyloxy, 2-Ethylhexyloxy, n-Octyloxy, n-Nonyloxy or n-Decyloxy.

Examples of cycloalkyl groups are those having five or six ring carbon atoms, which for their part may be substituted, for example with alkyl groups. An example of a cycloalkyl group is cyclohexyl.

Examples of cycloalkoxy groups are those with five or six ring carbon atoms in the cycloalkyl ring, which for their part may be substituted, for example with alkyl groups. An example of a cycloalkoxy group is cyclohexyloxy.

Examples of aryl groups are those having six or 10 carbon atoms in the aryl ring, which for their part may be substituted, for example with alkyl groups. An example of an aryl group is phenyl.

An example of an aralkyl group is benzyl, which for its part may be substituted, for example with alkyl groups.

An example of a carboxylic acid amide group is $C_1$-$C_4$-acylamino, preferably acetylamino.

The carbocyclic or heterocyclic aromatic compounds can have, in addition to aromatic rings, also non-aromatic saturated or ethylenically unsaturated rings, which are anellated to the aromatic rings, or are linked to the aromatic rings via covalent bonds or form a bicyclic or polycyclic systems with the aromatic rings.

Examples of particularly preferably used phenols are those derived from phenyl groups, substituted phenyl groups, naphthyl groups, substituted naphthyl groups, anthracenyl groups and substituted anthracenyl groups and which possess one phenolic hydroxyl group.

Particular preference is given to using phenols of formula (I)

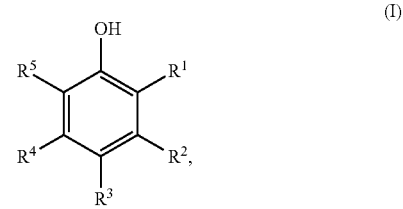

where $R^1$, $R^2$, $R^3$, $R^4$ and $R^5$ independently of one another are hydrogen, $C_1$-$C_{10}$-alkyl, $C_3$-$C_6$-cycloalkyl, $C_6$-$C_{10}$-aryl, $C_3$-$C_{10}$-heteroaryl having O, N and/or S as ring heteroatoms, $C_6$-$C_{10}$-aryl-$CH_2$, $C_6$-$C_{10}$-aryl-O, $C_1$-$C_{10}$-alkoxy, $C_3$-$C_8$-cycloalkoxy, N—$C_1$-$C_4$-alkylamino, N,N-di-$C_1$-$C_4$-alkylamino, $C_1$-$C_4$-acylamino, $COOR^6$ where $R^6$=hydrogen, $C_1$-$C_4$-alkyl or —$CH_2$—$R^7$ where $R^7$=hydroxyl, $C_1$-$C_4$-alkyloxy, N—$C_1$-$C_4$-alkylamino or N,N-di-$C_1$-$C_4$-alkylamino.

These phenols are hydrogenated by the method according to the invention with high selectivity to the corresponding cyclohexanones of the general formula (II)

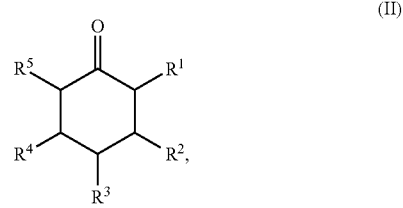

where $R^1$, $R^2$, $R^3$, $R^4$, $R^5$ have the meanings defined above.

In formulae (I) and (II), $R^1$, $R^2$, $R^3$, $R^4$ and $R^5$ independently of one another are preferably hydrogen, $C_1$-$C_6$-alkyl, $C_1$-$C_6$-alkoxy or $C_1$-$C_4$-acylamino, wherein 1 to 4 of the residues $R^1$ to $R^5$ are different from hydrogen.

With particular preference, $R^1$, $R^2$, $R^4$ and $R^5$ are hydrogen and $R^3$ is $C_1$-$C_{10}$-alkyl, $C_1$-$C_{10}$-alkoxy or $C_1$-$C_4$-acylamino.

The method described can be carried out in any reactor. Preferred examples thereof are stirred or loop reactors.

The hydrogenation times of the described method generally lie between one and three hours. However, shorter or longer reaction times can also be used in individual cases.

The selectivities achieved for cyclic ketones according to the method according to the invention are frequently above 94%, sometimes up to 96%.

The advantages of the method according to the invention lie in the fact that the range of usable solvents could be considerably broadened. Thus, it is possible to hydrogenate phenols, hitherto impractical due to poor solubilities or high melting points, in solution to give cyclic ketones. A further major advantage is that the catalysts used in the method described can be reused multiple times without resulting in loss of selectivity. This considerably reduces the use of precious metals and thus constitutes an enormous cost advantage.

A further major advantage is considered to be the fact that the method according to the invention can be carried out in the presence of water. By omitting costly drying steps, the productivity of the method is considerably increased.

The following examples illustrate the invention without limiting it.

EXAMPLES

The experiments were carried out with commercially available alkaline Pd/C catalysts (3% Pd/C, ca. 50% water moist). The raw materials and solvents used were supplied by the chemical industry.

Example 1

Preparation of 4-tert-butylcyclohexanone 250 g of 4-tert-butylphenol were dissolved in 135 g of tert-butanol, and 1.8 g of a sodium carbonate, lithium carbonate or sodium acetate or lithium acetate treated Pd/C catalyst and 2.4 g of water were added. The mixture was hydrogenated at 160° C./6 bar of hydrogen. The reaction was complete within 2 hours. The reaction solutions contained 89% of 4-tert-butylcyclohexanone.

Example 2

Preparation of 4-tert-butylcyclohexanone 250 g of 4-tert-butylphenol were dissolved in 135 g of tert-butanol, and 1.8 g of a potassium carbonate or cesium carbonate treated Pd/C catalyst were added. The mixture was hydrogenated at 160° C./6 bar of hydrogen. The reaction was complete within 2 hours. The reaction solutions contained 87% of 4-tert-butylcyclohexanone.

Example 3

Preparation of 4-tert-butylcyclohexanone 250 g of 4-tert-butylphenol were dissolved in 135 g of tert-amyl alcohol, and 1.8 g of a sodium carbonate, lithium carbonate or lithium acetate or sodium acetate treated Pd/C catalyst were added. The mixture was hydrogenated at 160° C./6 bar of hydrogen. The reaction was complete within 2 hours. The reaction solutions contained 87% of 4-tert-butylcyclohexanone.

Example 4

Preparation of 4-tert-butylcyclohexanone 250 g of 4-tert-butylphenol were dissolved in 135 g of 2-butanol, and 1.8 g of a sodium carbonate, lithium carbonate or lithium acetate or sodium acetate treated Pd/C catalyst and 2.4 g of water were added. The mixture was hydrogenated at 160° C./6 bar of hydrogen. The reaction was complete within 2 hours. The reaction solutions contained 91% of 4-tert-butylcyclohexanone.

Example 5

Preparation of 4-tert-butylcyclohexanone 300 g of 4-tert-butylphenol were dissolved in 125 g of 4-methylpentan-2-ol, and 2.9 g of a sodium carbonate, lithium carbonate or sodium acetate or lithium acetate treated Pd/C catalyst were added. The mixture was hydrogenated at 160° C./6 bar of hydrogen. The reaction was complete within 1 hour. The reaction solutions contained 94 to 96% of 4-tert-butylcyclohexanone.

Example 6

Preparation of 4-methoxycyclohexanone 250 g of 4-methoxyphenol were hydrogenated within 1.7 hours in 125 g of tert-butanol at 150° C./5 bar of hydrogen over 2.9 g of a Pd/C catalyst which had been treated with sodium carbonate or lithium carbonate or sodium acetate or lithium acetate. The hydrogenation solution contained 93% of 4-methoxycyclohexanone.

Example 7

Preparation of 4-methoxycyclohexanone 250 g of 4-methoxyphenol were hydrogenated over the course of 3 h in 125 g of 4-methylpentan-2-ol at 140° C./4 bar of hydrogen over a lithium carbonate or sodium carbonate or lithium acetate or sodium acetate treated Pd/C catalyst. In the hydrogenation solution 92% to 94% of 4-methoxycyclohexanone were present.

Example 8

Preparation of 4-methylcyclohexanone 250 g of p-cresol were dissolved in 130 g of 2-butanol and hydrogenated at 170° C./6 bar of hydrogen over 3.2 g of a lithium carbonate or sodium carbonate or lithium acetate or sodium acetate treated Pd/C catalyst. The hydrogenation time was 3 h. The reaction solution contained 93% of 4-methylcyclohexanone.

Example 9

Preparation of 3-methylcyclohexanone 250 g of m-cresol were dissolved in 144 g of 4-methylpentan-2-ol and hydrogenated over the course of 1.5 hours at 170° C./6 bar of hydrogen over 3.3 g of a sodium carbonate or lithium carbonate or sodium acetate or lithium acetate treated Pd/C catalyst. The reaction mixture contained 96% of 3-methylcyclohexanone.

Example 10

Preparation of 2-methylcyclohexanone 250 g of o-cresol were dissolved in 144 g of 4-methylpentan-2-ol and hydrogenated at 170° C./6 bar of hydrogen over 3.3 g of a sodium carbonate or lithium carbonate or sodium acetate or lithium acetate treated Pd/C catalyst. The hydrogenation time was 3.5 hours. In the reaction solution 95% of 2-methylcyclohexanone was detected.

Example 11

Preparation of 4-methylcyclohexanone 250 g of p-cresol were dissolved in 142 g of pentan-2-ol and hydrogenated at 160° C./6 bar of hydrogen over 3.3 g of a sodium carbonate or lithium carbonate or sodium acetate or lithium acetate treated Pd/C catalyst. The reaction time was 2.5 hours; in the reaction solution 94% of 4-methylcyclohexanone were present.

Example 12

Preparation of 4-methylcyclohexanone 250 g of p-cresol were dissolved in 144 g of cyclohexanol and hydrogenated at 160° C./6 bar of hydrogen over 3.3 g of a sodium carbonate or lithium carbonate or sodium acetate or lithium acetate treated Pd/C catalyst. After a hydrogenation time of 3 h the reaction mixture contained 91% of 4-methylcyclohexanone.

Example 13

Preparation of 4-methoxycyclohexanone 250 g of 4-methoxyphenol were dissolved in 125 g of 4-methylpentan-2-ol and hydrogenated at 140° C./3.5 bar of hydrogen over 3.7 g of a recycled Pd/C catalyst, which had been treated only before its first use with sodium carbonate or lithium carbonate or sodium acetate or lithium acetate. After a hydrogenation time of 4.7 h, 92% of 4-methoxycyclohexanone were present in the reaction solution.

Example 14

Preparation of 4-tert-butylcyclohexanone 300 g of 4-tert-butylphenol were dissolved in 125 g of 4-methylpentan-2-ol and hydrogenated at 160° C./6 bar of hydrogen over 4.0 g of a recycled Pd/C catalyst, which had been treated only before its first use with sodium carbonate or lithium carbonate or sodium acetate or lithium acetate. The hydrogenation time was 3.5 h. The reaction mixture contained 94% of 4-tert-butylcyclohexanone.

Example 15

Preparation of 4-tert-butylcyclohexanone 300 g of 4-tert-butylphenol were dissolved in 125 g of 4-methylpentan-2-ol and hydrogenated at 160° C./6 bar of hydrogen over 2.9 g of a sodium tetraborate pre-treated Pd/C catalyst. The hydrogenation time was 50 min; in the reaction mixture 89% of 4-tert-butylcyclohexanone were present.

Example 16

Preparation of 4-tert-butylcyclohexanone 300 g of tert-butylphenol were dissolved in 125 g of 4-methylpentan-2-ol and hydrogenated at 160° C./6 bar of hydrogen over 1.7 g of a Pd/C catalyst treated with basic magnesium carbonate and sodium carbonate. The hydrogenation time was 1.3 h. The reaction mixture contained 93% of 4-tert-butylcyclohexanone.

Comparative Examples

Example 17

Hydrogenation Over a Non-Alkalized Catalyst 250 g of 4-methoxyphenol were dissolved in 125 g of 4-methylpentan-2-ol and hydrogenated at 140° C./3.5 bar of hydrogen over 2.9 g of a Pd/C catalyst not previously treated with a basic or neutral salt. After a hydrogenation time of 5 hours, 77% of 4-methoxycyclohexanone were present in the reaction solution.

Example 18

Hydrogenation in Isooctane 20 kg of tert-butylphenol, dissolved in 20 kg of isooctane, were hydrogenated over the course of 3 h over 0.071 g of a sodium carbonate alkalized dried Pd/C catalyst at 150° C./5 bar of hydrogen. In the reaction mixture 80% of 4-tert-butylcyclohexanone were detected.

If the catalyst was used 50% water-moist, i.e. in the commercially available form, then it clumped together. No hydrogen absorption took place.

While the invention has been described in detail, modifications within the spirit and scope of the invention will be readily apparent to those of skill in the art. In view of the foregoing discussion, relevant knowledge in the art and references discussed above in connection with the Background, the disclosures of which are all incorporated herein by reference, further description is deemed unnecessary. In addition, it should be understood that aspects of the invention and portions of various embodiments may be combined or interchanged either in whole or in part.

Furthermore, those of ordinary skill in the art will appreciate that the foregoing description is by way of example only, and is not intended to limit the invention.

The invention claimed is:

1. A method for hydrogenating phenols with one hydroxyl group to cyclic ketones by reacting the phenols with hydrogen in the presence of a catalyst in a solution comprising an aliphatic and/or cycloaliphatic alcohol with at least three carbon atoms, wherein a supported catalyst comprising palladium is used, which has been treated prior to use with a neutral or basic salt, and/or wherein the hydrogenation takes place in the presence of a supported catalyst comprising palladium and a neutral or basic salt, with the proviso that the use of catalysts comprising palladium and inorganic sulfur compounds and/or organic sulfur compounds is excluded.

2. The method as claimed in claim 1 wherein the reaction takes place at temperatures of 80 to 250° C.

3. The method as claimed in claim 1 wherein the reaction takes place at a hydrogen pressure of 0.5 to 20 bar.

4. The method as claimed in claim 1, wherein a straight-chain or branched secondary or tertiary aliphatic alcohol with at least three carbon atoms is used as the aliphatic alcohol with at least three carbon atoms.

5. The method as claimed in claim 1, wherein the reaction takes place in an aqueous alcoholic solution, the water content of which is up to 20% by weight, based on the total amount of solvent.

6. The method as claimed in claim 1, wherein the concentration of the phenol in the aliphatic and/or cycloaliphatic alcohol is 10 to 95% by weight.

7. The method as claimed in claim 1, wherein the supported catalyst comprising palladium used is a palladium catalyst supported on carbon.

8. The method as claimed in claim 1, wherein the supported catalyst comprising palladium comprises 1 to 15% by weight of catalytically active metal.

9. The method as claimed in claim 1, wherein the supported catalyst comprising palladium is treated prior to use with a neutral or basic salt.

10. The method as claimed in claim 9, wherein the neutral or basic salt is an hydroxide, carbonate, hydrogen carbonate, phosphate, monohydrogen phosphate, formate, acetate, propionate or borate of lithium, sodium, potassium, rubidium, cesium, beryllium, magnesium, calcium, strontium, barium or ammonium.

11. The method as claimed in claim 1, wherein the supported palladium catalyst is used in amounts of $1\times10^{-4}$ to 1% by weight (calculated in each case as Pd metal), based on the phenol used.

12. The method as claimed in claim 1, wherein the supported palladium catalyst used is fresh or has already been used once or more than once.

13. The method as claimed in claim 1, wherein the neutral or basic salt added to the catalyst is added in amounts of 0.001-5 mol %, based on the phenol used.

14. The method as claimed in claim 1, wherein a compound of formula (I) is used as the phenol

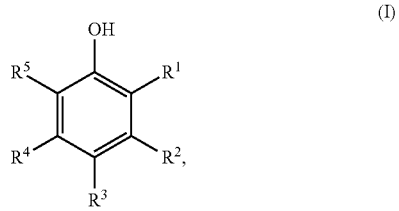

where $R^1$, $R^2$, $R^3$, $R^4$, $R^5$ independently of one another are hydrogen, $C_1$-$C_{10}$-alkyl, $C_3$-$C_6$-cycloalkyl, $C_6$-$C_{10}$-aryl, $C_3$-$C_{10}$-heteroaryl with 0, N and/or S as ring heteroatoms, $C_6$-$C_{10}$-aryl-$CH_2$, $C_6$-$C_{10}$-aryl-O, $C_1$-$C_{10}$-alkoxy, $C_3$-$C_8$-cycloalkoxy, N—$C_1$-$C_4$-alkylamino, N,N-di-$C_1$-$C_4$-alkylamino, $C_1$-$C_4$-acylamino, COOR$^6$ where R$^6$=hydrogen, $C_1$-$C_4$-alkyl or —$CH_2$—R$^7$ where R$^7$=hydroxyl, $C_1$-$C_4$-alkyloxy, N—$C_1$-$C_4$-alkylamino or N,N-di-$C_1$-$C_4$-alkylamino.

15. The method as claimed in claim 1 wherein the reaction takes place at temperatures of 100 to 180° C.

16. The method as claimed in claim 1 wherein the reaction takes place at a hydrogen pressure of 1 to 10 bar.

17. The method as claimed in claim 1 wherein a straight-chain or branched secondary or tertiary aliphatic alcohol with three to eight carbon atoms is used as the aliphatic alcohol with at least three carbon atoms.

18. The method as claimed in claim 1 wherein the aliphatic alcohol with at least three carbon atoms is selected from the group consisting of isopropanol, 2-butanol, tert-butanol, 2-pentanol, 3-pentanol, 2-methylbutan-2-ol, 3-methylbutan-2-ol, cyclopentanol, cyclohexanol, 2-methylpentan-2-ol, 2-methylpentan-3-ol, 3-methylpentan-2-ol, 3-methylpentan-3-ol, 4-methylpentan-2-ol, 2,3-dimethyl-2-butanol, 3,3-dimethyl-2-butanol, 2-hexanol, 3-hexanol, 2,2-dimethyl-3-pentanol, 2,3-dimethyl-3-pentanol, 2,4-dimethyl-3-pentanol, 4,4-dimethyl-2-pentanol, 3-ethyl-3-pentanol, 2-methyl-2-hexanol, 2-methyl-3-hexanol, 5-methyl-2-hexanol, 2-heptanol, 3-heptanol, 2-octanol, 3-octanol, 4-methylheptan-3-ol, 6-methylheptan-2-ol, 2-ethylhexanol and 3,7-dimethyl-3-octanol.

19. The method as claimed in claim 1 wherein the supported catalyst comprising palladium is treated prior to use with a neutral or basic aqueous solution of an alkali metal salt, alkaline earth metal salt or ammonium salt.

20. The method as claimed in claim 1 wherein a compound of formula (I) is used as the phenol

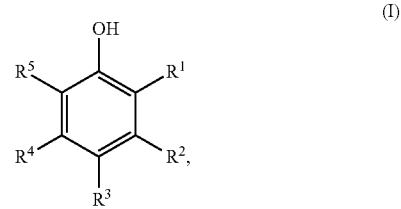

where R1, R2, R3, R4 and R5, independently of one another, are hydrogen, C1-C10-alkyl, C1-C10-alkoxy or C1-C4-alkylamino and one to four of these residues are different from hydrogen.

* * * * *